United States Patent
Sun et al.

(10) Patent No.: US 10,357,032 B2
(45) Date of Patent: Jul. 23, 2019

(54) MACROSTRUCTURE FORMING SURFACTANTS USEFUL AS SPRAY DRIFT CONTROL AGENTS IN PESTICIDE SPRAYING APPLICATIONS

(71) Applicants: AKZO NOBEL CHEMICALS INTERNATIONAL B.V., Arnhem (NL); DOW AGROSCIENCES LLC, Indianapolis, IN (US)

(72) Inventors: Jinxia Susan Sun, Hopewell Junction, NY (US); Shawn Zhu, Stormville, NY (US); Martin W. Murray, Guisborough Cleveland (GB); Marcus Boone, Savannah, GA (US); Michael Walters, Rhinebeck, NY (US); Qingwen Wendy Yuan-Huffman, Belle Mead, NJ (US); Christine Puglisi, Mountainside, NJ (US); Brandon Matthew Downer, Lebanon, IN (US); Stephen L. Wilson, Zionsville, IN (US)

(73) Assignees: AKZO NOBEL CHEMICALS INTERNATIONAL B.V., Amersfoort (NL); DOW AGROSCIENCES LLC, Indianapolis, IN (US)

( * ) Notice: Subject to any disclaimer, the term of this patent is extended or adjusted under 35 U.S.C. 154(b) by 3 days.

(21) Appl. No.: 15/869,217

(22) Filed: Jan. 12, 2018

(65) Prior Publication Data

US 2018/0132480 A1    May 17, 2018

Related U.S. Application Data

(62) Division of application No. 14/369,022, filed as application No. PCT/EP2012/076535 on Dec. 21, 2012, now Pat. No. 9,888,683.

(60) Provisional application No. 61/648,105, filed on May 17, 2012, provisional application No. 61/581,395, filed on Dec. 29, 2011.

(51) Int. Cl.

| *A01N 25/30* | (2006.01) |
|---|---|
| *A01N 25/06* | (2006.01) |
| *A01N 57/20* | (2006.01) |
| *A01N 39/04* | (2006.01) |
| *A01N 37/38* | (2006.01) |

(52) U.S. Cl.
CPC ............ *A01N 25/30* (2013.01); *A01N 25/06* (2013.01); *A01N 37/38* (2013.01); *A01N 39/04* (2013.01); *A01N 57/20* (2013.01)

(58) Field of Classification Search
USPC .................................................. 504/127, 317
See application file for complete search history.

(56) References Cited

U.S. PATENT DOCUMENTS

| 2,771,477 A | 11/1956 | De Afley et al. |
|---|---|---|
| 3,373,107 A | 3/1968 | Rice et al. |
| 4,770,814 A | 9/1988 | Rose et al. |
| 4,844,734 A | 7/1989 | Iwasaki et al. |
| 5,550,224 A | 8/1996 | Hazen |
| 5,863,863 A | 1/1999 | Hasebe et al. |
| 8,993,629 B2 | 3/2015 | Sun |
| 2004/0213751 A1 | 10/2004 | Schwartz et al. |
| 2005/0130842 A1 | 6/2005 | Fleute-Schlachter et al. |
| 2006/0025321 A1 | 2/2006 | Treybig et al. |
| 2009/0270258 A1 | 10/2009 | Rose et al. |
| 2010/0009937 A1 | 1/2010 | Elsik et al. |
| 2011/0166235 A1 | 7/2011 | Sun |
| 2012/0065068 A1 | 3/2012 | Downer et al. |
| 2013/0260998 A1 | 10/2013 | Zhu et al. |
| 2014/0179529 A1 | 6/2014 | Downer et al. |
| 2015/0201612 A1 | 7/2015 | Sun |
| 2016/0081332 A1 | 3/2016 | Zhu et al. |
| 2016/0205926 A1 | 7/2016 | Downer et al. |

FOREIGN PATENT DOCUMENTS

| CN | 101267733 A | 9/2008 |
|---|---|---|
| CN | 102170781 A | 8/2011 |
| CN | 103209591 A | 7/2013 |
| EP | 0 274 369 A1 | 7/1988 |
| JP | S 54 147929 A | 11/1979 |
| JP | S 63 022502 A | 1/1988 |
| JP | S 63 145205 A | 6/1988 |

(Continued)

OTHER PUBLICATIONS

Fife, Bruce; "Coconut Cures: Preventing and Treating Common Health Problems with Coconut"; Published 2005; books.google.com.

*Primary Examiner* — Ali Soroush
*Assistant Examiner* — Courtney A Brown
(74) *Attorney, Agent, or Firm* — Norris McLaughlin, P.A.

(57) ABSTRACT

The present invention relates to an aqueous agrochemical spray solution containing an agrochemical active and a surfactant. The spray solution comprises a dispersed phase comprising dispersed particles which have an average particle size between 1 to 100 microns and the concentration of said dispersed particles is from about 0.001 to 5 wt %. The aqueous agrochemical spray solution is capable of reducing the volume of the fine droplets in mist whose size is less than 150 microns during spraying by at least 20% compared to the same aqueous spray solution without the presence of the surfactant. The present invention also relates to a method of reducing the spray drift of an aqueous agrochemical spray solution upon spraying with a spraying apparatus. The method includes adding the surfactant to the aqueous agrochemical spray solution in an amount effective to form the dispersed phase.

15 Claims, 2 Drawing Sheets

(56) References Cited

FOREIGN PATENT DOCUMENTS

| | | |
|---|---|---|
| JP | H 07 285810 A | 10/1995 |
| JP | H 10 505362 A | 5/1998 |
| JP | 2012 056926 A | 3/2012 |
| JP | 2013 537230 A | 9/2013 |
| RU | 2 364 085 C2 | 8/2009 |
| WO | 97 01281 A1 | 1/1997 |
| WO | 01 89302 A2 | 11/2001 |
| WO | 2009 148570 A1 | 12/2009 |
| WO | 2010 020599 A3 | 2/2010 |
| WO | 2010 026127 A1 | 3/2010 |
| WO | 2012 037207 A1 | 3/2012 |
| WO | 2012 076567 A2 | 6/2012 |

FIG. 2. Vol.% of droplets < 150 mm in spray drift (room temp)

MACROSTRUCTURE FORMING SURFACTANTS USEFUL AS SPRAY DRIFT CONTROL AGENTS IN PESTICIDE SPRAYING APPLICATIONS

PRIORITY CLAIM

This application is a division of U.S. Non-provisional application Ser. No. 14/369,022, filed Jun. 26, 2014, now pending, which is a 371 of International Patent Application No. PCT/EP2012/076535, filed Dec. 21, 2012, which claims priority benefit of U.S. Provisional Application No. 61/648,105, filed May 17, 2012, and U.S. Provisional Application No. 61/581,395, filed Dec. 29, 2011, the disclosures of which patent applications are incorporated herein by reference.

FIELD OF THE INVENTION

The present invention relates to a surfactant composition and a method capable of forming a dispersion system with macrostructures in aqueous environment resulting in reduced number of fine droplets in mist during spraying agricultural pesticide solutions when the size of the dispersed particles is between 1-100 µm and the concentration of the dispersed particles is between 0.001-5 wt %.

BACKGROUND OF THE INVENTION

The drift of spray from pesticide applications can expose people, wildlife, and the environment to pesticide residues that can cause health and environmental effects and property damage. Spray drift can prevent a substantial portion of the pesticide from reaching its intended target, requiring more of the pesticide to achieve adequate coverage of the target.

In practice, two chemical approaches have been used to reduce the amount of drifting of small droplets during spraying of an aqueous pesticide solution.

In the first approach, high molecular weight water soluble polymers such as a guar gum, xanthan gum, polyacrylamides, polyethylene oxide, and other ethylenically unsaturated monomers are employed as drift control agents in the agricultural application. It has been generally accepted that polymers which give optimum spray drift control are either non-ionic (e.g., acrylamide homopolymer) or have relatively low anionic content (e.g. 5 to 30 wt. %) and also have relatively high intrinsic viscosity, for instance above 6 dl/g. Guar gum is one of the most widely used drift control agent in the current world market. It is believed that the polymers produce an enhanced extensional viscosity during spraying which is the main reason for the improved drift control over spraying water. Unfortunately, these polymers have various drawbacks. One drawback is that their solutions tend to show irreversible lose of their utility due to the fact that high molecular weight polymers undergo mechanical degradation of the polymer chain. Another drawback is that it takes a long time for the high molecular weight polymers to evenly disperse or dissolve in aqueous liquids which may lead to many large and undissolved particles that could plug the spraying nozzle. Still another drawback of polymers as drift control agents is that the polymers are difficult to build into a high salt premix pesticide formulation without gelling or phase separation. In addition, the polymer drift control agents perform mainly one task—to control drift of small droplets during spraying.

In the second approach, a crop oil concentrate (COC) is employed which contains an emulsifier and a hydrophobic substance such as a mineral oil or a methyl ester. COC can forms oil-in-water (o/w) emulsions upon dilution in water which can reduce the fine droplets during spraying, hence for its application as a drift control agent. However, COC is not recommended if the agrochemical formulation is a herbicide and contains a water soluble salts as the active ingredients such as isopropylamine salt of glyphosate because COC may reduce the efficacy of the active ingredient.

Spray pattern plays an important role in small droplets drifting. When water is sprayed, many small liquid droplets form a mist which easily drifts away with wind. When an aqueous spraying solution containing a drift control agent such as guar gum is sprayed, the sprayed pattern is modified so that the number of small droplets is much reduced. Reduction of the number of small droplets increases the size of the droplets when the spray volume remains the same. In fact, the size increase in a typical spraying solution containing guar gum as the drift control agent is often too much so that there are a lot of coarse droplets which tend to bounce off the plant leave and be wasted. Over the years, researchers have discovered that the optimum spray pattern has a droplet size distribution between 100-400 µm.

It is the object of the claimed invention to provide a surfactant composition and a method capable of forming a dispersion system with macrostructures in aqueous environment resulting in reduced number of fine droplets in mist during spraying agricultural pesticide solutions, wherein the size of the dispersed particles is between 1-100 µm and the concentration of the dispersed particles is between 0.001-5 wt %.

SUMMARY OF THE INVENTION

The present invention relates to a surfactant composition and a method capable of forming a dispersion system with macrostructures in aqueous environment resulting in reduced number of fine droplets in mist during spraying agricultural pesticide solutions, wherein the size of the dispersed particles is between 1-100 µm and the concentration of the dispersed particles is between 0.001-5 wt %.

The present invention also relates to an agrochemical formulation comprising an active ingredient and at least one surfactant, wherein the said agrochemical formulation is capable of forming a aqueous agrochemical spray solution containing a dispersed phase comprising dispersed particles which have an average particle size between 1 to 100 microns, wherein the concentration of said dispersed particles is from about 0.001 to 5 wt %, and wherein said aqueous spray solution is capable of reducing the volume of the fine droplets in mist whose size is less than 150 microns during spraying by at least 20% compared to the same aqueous spray solution without the presence of the said surfactant.

The present invention further relates to an aqueous agrochemical spray solution comprising at least one agrochemical active and at least one surfactant, wherein said spray solution comprises a dispersed phase comprising dispersed particles which have an average particle size between 1 to 100 microns, wherein the concentration of said dispersed particles is from about 0.001 to 5 wt %, and wherein said aqueous agrochemical spray solution is capable of reducing the volume of the fine droplets in mist whose size is less than 150 microns during spraying by at least 20% compared to the same aqueous spray solution without the presence of the said surfactant.

The present invention also relates to a method of reducing the spray drift of an aqueous agrochemical spray solution upon spraying with a spraying apparatus, which comprises adding at least one surfactant to said aqueous agrochemical spray solution in an amount effective to form a dispersed phase comprising dispersed particles which have an average particle size between 1 to 100 microns, wherein the concentration of said dispersed particles is from about 0.001 to 5 wt %, and wherein said aqueous spray solution is capable of reducing the volume of the fine droplets in mist whose size is less than 150 microns during spraying by at least 20% compared to the same aqueous spray solution without the presence of the said surfactant.

BRIEF DESCRIPTION OF THE DRAWINGS

The invention will be described in greater detail with reference to the drawings, wherein:

FIG. 2 is a phase diagram plotting the results of Table 5.

DETAILED DESCRIPTION OF THE INVENTION

Figure 1:
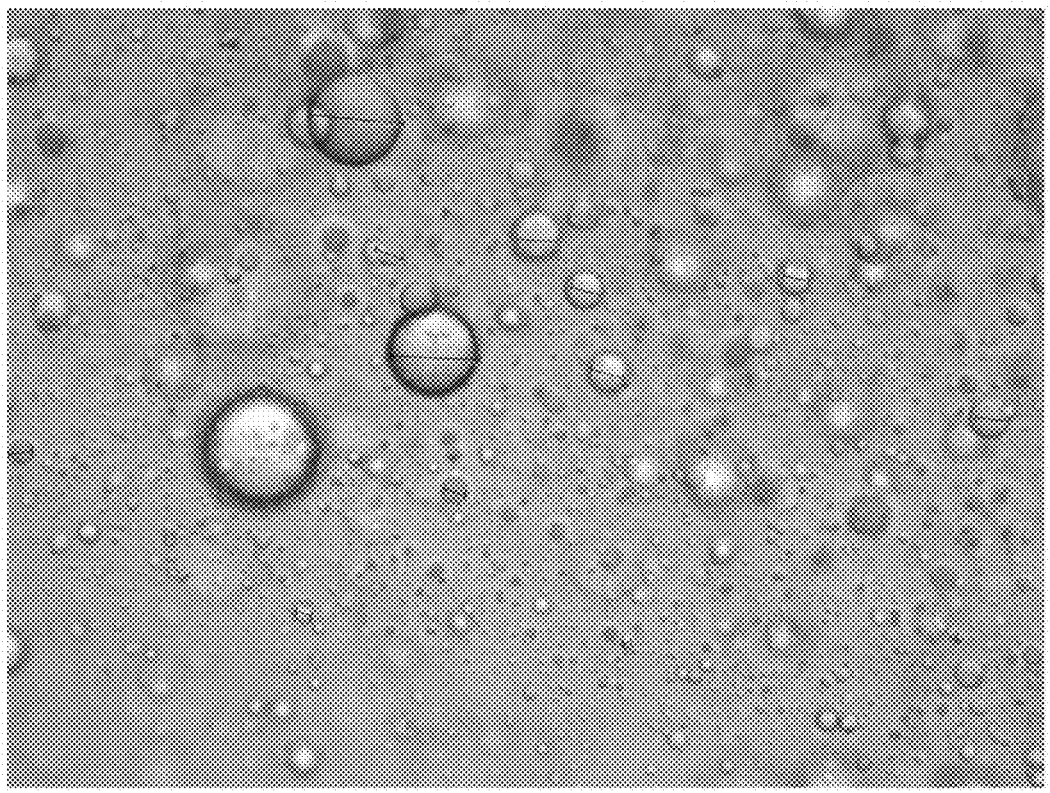
FIG. 1 is a photograph showing the microstructure captured for sample #1 in Table 5.

One embodiment of the present invention relates to a ready to spray agrochemical formulation, wherein said agrochemical formulation is a dispersion comprising a pesticide, a surfactant, and water capable of reducing drift during spraying.

Another embodiment of the present invention relates to a concentrated agrochemical formulation comprising a pesticide and a surfactant, wherein said concentrated agrochemical formulation is capable of forming a dispersion when diluted in water, wherein said dispersion is capable of reducing drift during spraying. The concentrated agrochemical formulation can be a solid formulation, a clear liquid formulation, or a stable turbid liquid formulation.

Still another embodiment of the present invention relates to a surfactant capable of forming a dispersion when added into a spray tank to form the ready to spray aqueous agrochemical formulation, wherein said dispersion is capable of reducing drift during spraying.

Specifically, in the above mentioned embodiments the said dispersion is characterized in having a dispersed particle size from 1-100 μm and a concentration of the dispersed particles from about 0.001% to 5 wt %, in another embodiment from about 0.001% to 0.1%, still in another embodiment from about 0.01% to 1%, and yet still in another embodiment from 1% to 3%, and wherein said formulation is capable of reducing the volume of the fine droplets in mist whose size is less than 150 μm during spraying the said dispersion by at least 20%. In one embodiment, the said dispersion is characterized in having a dispersed particle size from 2-20 μm (in another embodiment, 20-60 μm) and a concentration of the dispersed particles from 0.001 to 5 wt %, in another embodiment from about 0.001 to 0.1%, still in another embodiment from about 0.01 to 1%, and yet still in another embodiment from 1 to 3%, and wherein said formulation is capable of reducing the volume of the fine droplets in mist whose size is less than 150 μm during spraying the said dispersion by at least 20%. In another embodiment, the said dispersion is characterized in having a dispersed particle size from 5-10 μm (in yet another embodiment, 4-40 μm) and a concentration of the dispersed particles from 0.001 to 5 wt %, in another embodiment from about 0.001 to 0.1 wt %, still in another embodiment from about 0.01 to 1 wt %, and yet still in another embodiment from 1 to 3 wt %, and wherein said formulation is capable of reducing the volume of the fine droplets in mist whose size is less than 150 μm during spraying the said dispersion by at least 20%. The said at least 20% reduction in volume of the fine droplets in mist during spraying is achieved by having the said surfactant in the formulation.

The preferred dispersion system is substantially free of crop oils used in COC.

The dispersed particles in the dispersion system are typically vesicles or liposomes. The dispersed particles may trap additives, if present, in it. However, preferably it is substantially free of crop oils used in COC. The size distribution of the dispersed particles, throughout the context, is an average number and can be bimodal or multimodal. We discovered that both the size and amount of dispersed particles are important in spray drift control. That is the presence of dispersed particles is necessary for the dispersion system to exhibit good anti-drift property and the concentration of dispersed particles plays an important role in determining the fine droplets amount during spraying. If there are too many dispersed particles, there is little or no reduction in spray drift. If there are too few dispersed particles, typically indicated by the clarity of the solution, the anti-drift performance is also not good. Only when the number and size of dispersed particles are properly balanced spray drift reduction is significant.

Typically, spray solutions meeting the above criteria are characterized by the presence of haziness.

Throughout the context, the surfactant means a single surfactant, a blend of surfactants, or a surfactant composition comprising a surfactant, a polymer such as guar gum or a cellulosic derived polymer, diluents such as water or glycols, or other additives. An added benefit is that certain surfactants can provide additional adjuvancy to the pesticide system.

Surfactants employable in this regard include, but are not limited to cationic or quaternary surfactants, nonionic surfactants, amphoteric surfactants, anionic surfactants, and all known surfactants in the industry including silicone surfactants, polymeric surfactants, and fluoral surfactants. Not all surfactants in each category are suitable and even with a suitable surfactant, it has to meet the criteria. Non-limiting examples of useful surfactant according to the present invention are: di-tallow dimethyl quaternary surfactants, preferably di-tallow dimethyl chloride, C16-C22 amine ethoxylate with 2EO and its oxide and betaine, C16-C22 amine ethoxylate quaternary with 2 EO, C12-C22 dimethylaminopropyl amine and its oxide and betaine, C12-C18 dimethyl amine oxide, C12-C18 dimethyl betaine, and C12-C18 amidoamine ethoxylate derived from DETA (diethylenetriamine) and its oxide and betaine; preferably the hydrocarbon chains are derived from coco, tallow, soy, corn, castor, coconut, palm, canola, lard, peanut, or tall oil fatty acid mentioned previously.

In one embodiment, the surfactant is a nitrogen containing surfactant. The nitrogen containing surfactant may be di-alkyl di-methyl quaternary surfactant with a counterion of chloride, bromide, methylsulfate, carbonate, or bicarbonate; an alkyl dimethylamidopropylamine; an alkyl dimethylamidopropylamine oxide or alkyl dimethylamidopropylamine betaine; an alkyl amidoamine ethoxylate wherein the alkyl amidoamine ethoxylate is a product derived from alkyl fatty acid and diethylenetriamine followed by ethoxylation; an alkyl di-ethoxylated with 2EO methyl chloride quaternary surfactant. The alkyl group in the above-mentioned nitrogen containing surfactant is C12-C22 (in one embodiment, C16-

C22), saturated or non-saturated, linear or branched alkyl group derived from oil of coco, soy, palm, castor, tallow, corn, lard, peanut or tall, including the epoxydized version of the oil.

The nitrogen containing surfactant may also be a tertiary amine surfactant of the formula:

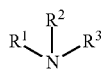

wherein $R^1$ represents a straight or branched chain ($C_{12}$-$C_{22}$) alkyl and $R^2$ and $R^3$ independently represent a straight or branched chain ($C_1$-$C_{22}$) alkyl. Further, the nitrogen containing surfactant may also be a tertiary amine oxide surfactant of the formula:

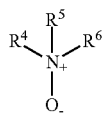

wherein $R^4$ is a straight or branched chain ($C_{10}$-$C_{22}$) alkyl or an alkyletherpropyl, and $R^5$ and $R^6$ independently are straight or branched chain ($C_1$-$C_{22}$) alkyl or ethoxylates or propoxylates of the formula:

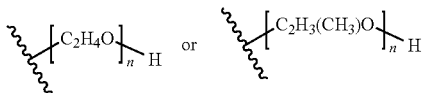

wherein n is an integer from 1 to 20. In one embodiment, the tertiary amine oxide is coco dimethyl aminoxide.

Furthermore, the nitrogen containing surfactant may be an alkoxylated aminoxide derived from alkoxylated alkylamine, wherein the alkyl group is C12-C22, saturated or non-saturated, linear or branched alkyl group derived from oil of coco, soy, palm, castor, tallow, corn, lard, peanut or tall, including the epoxydized version of the oil. In one embodiment, the alkoxylated aminoxide is an ethoxylated alkyl aminoxide with two ethoxylation units (2EO).

The nitrogen containing surfactant may also be an alkoxylated amide. The alkoxylated amide may be a reaction product of fatty acid with diethanolamine. Further, the alkoxylated amide may be ethoxylated with 2-20 ethoxylation units.

Alternatively, the alkoxylated amide may be a reaction product of fatty acid with monoethanolamine, which may also be ethoxylated with 2-20 ethoxylation units.

Because of the presence of a dispersed particle phase, the spray solution typically has a haze or turbidity in it. In other words, a clear spray solution will generally not have good drift control property. Correlating the haziness with good drift control is a very helpful and important tool. This discovery provides a convenient tool for farmers to judge whether the drift control agents they have added to the spray tank work or not because they can simply look at the spray solution appearance and know the result without doing complicated experiment. This discovery is also important for a formulator who is developing drift control formulations. The presence of haziness in a spray solution is a necessary condition for a good drift control.

The compositions of the invention can be prepared in the manner known to the skilled artisan, including but not limited to in-can and tank mix and application of the final formulation may be pre- or post-emergence. Post-emergence application results in particular advantages.

In one embodiment, the agrochemical formulation is a herbicide formulation having improved drift control comprising the surfactant drift control agent in accordance with the invention. Examples of suitable herbicides include, but are not limited to:

acetochlor, acifluorfen, aclonifen, alachlor, ametryn, amidosulfuron, aminopyralid, amitrole, anilofos, asulam, atrazine, azafenidin, azimsulfuron, benazolin, benfluralin, bensulfuron-methyl, bentazone, bifenox, binalafos, bispyribac-sodium, bromacil, bromoxynil, butachlor, butroxidim, cafenstrole, carbetamide, carfentrazone-ethyl, chloridazon, Chlorimuron-ethyl, chlorobromuron, chlorotoluron, chlorsulfuron, cinidon-ethyl, cinosulfuron, clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Flurochloridone, Fluroxypyr, Flurtamone, Fomesafen, Foramsulfuron, Glyphosate, Glufosinate, Hexazinone, Imazamethabenz-m, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. Preferred herbicides are Acetochlor, Atrazine, Dicamba, Glufosinate, Paraquat, and mixtures and combinations thereof. More preferred herbicides are glyphosate, Atrazine, Dicamba, and Glufosinate and mixtures and combinations thereof. The most preferred herbicides are salts of glyphosate and glufosinate-ammonium. When the herbicide is an acid, it can be used in the acid form, though it is preferred that the herbicide be in the salt form selected from at least one of the group of an amine, lithium, sodium, ammonium or potassium. It shall be pointed out that when a pesticide appears in the text as a general name without specifying the counterions, it means both its acid form and salt form throughout the context.

In another embodiment, the agrochemical formulation is a fungicide formulation having improved drift control comprising the surfactant drift control agent in accordance with the invention. Examples of suitable fungicides include, but are not limited to: Acibenzolar-S-methyl, aldimorph, amisulbrom, anilazine, azaconazole, azoxystrobin, benalaxyl, benodanil, benomyl, benthiavalicarb, binapacryl, biphenyl, bitertanol, blasticidin-S, boscalid, bromuconazole, bupirimate, captafol, captan, carbendazim, carboxin, carpropamid, chloroneb, chlorothalonil, chlozolinate, copper, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, dinocap, dithianon, dodemorph, dodine, edifenphos, enestrobin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluoxastrobin, fluquinconazole, flusilazole, flusulfamide, flutolanil, flutriafol, folpet, fosetyl-Al, fthalide, fuberidazole, furalaxyl, furametpyr, guazatine, hexaconazole, hymexazole, imazalil, imibenconazole, iminoctadine, iodocarb, ipconazole, iprobenfos (IBP), iprodione, iprovalicarb, isoprothiolane, isotianil, kasugamycin, kresoxim-methyl, laminarin, mancozeb, mandipropamid, maneb, material of biological, mepanipyrim, mepronil, meptyldinocap, metalaxyl, metalaxyl-M, metconazole, methasulfocarb, metiram, metominostrobin, metrafenone, mineral oils, organic oils, myclobutanil, naftifine, nuarimol, octhilinone, ofurace, origin, orysastrobin, oxadixyl, oxolinic acid, oxpoconazole, oxycarboxin, oxytetracycline, pefurazoate, penconazole, pencycuron, penthiopyrad, phophorous acid and, picoxystrobin, piperalin, polyoxin, potassium bicarbonate, probenazole, prochloraz, procymidone, propamocarb, propiconazole, propineb, proquinazid, prothiocarb, prothioconazole, pyraclostrobin, pyrazophos, pyribencarb, pyributicarb, pyrifenox, pyrimethanil, pyroquilon, quinoxyfen, quintozene (PCNB), salts, silthiofam, simeconazole, spiroxamine, streptomycin, sulphur, tebuconazole, teclofthalam, tecnazene (TCNB), terbinafine, tetraconazole, thiabendazole, thifluzamide, thiophanate, thiophanate-methyl, thiram, tiadinil, tolclofosmethyl, tolylfluanid, triadimefon, triadimenol, triazoxide, tricyclazole, tridemorph, trifloxystrobin, triflumizole, triforine, triticonazole, validamycin, valiphenal, vinclozolin, zineb, ziram, and zoxamide, and mixtures and combinations thereof Still another embodiment of the present invention is an insecticide formulation having improved drift control comprising the surfactant drift control agent in accordance with the invention. Examples of suitable insecticides include, but are not limited to: kerosene or borax, botanicals or natural organic compounds (nicotine, pyrethrin, strychnine and rotenone), chorinated hydrocarbon (DDT, lindane, chlordane), organophosphates (malathion and diazinon), carbamates (carbaryl and propoxur), fumigants (naphthalene) and benzene (mothballs), synthetic pyrethroids, and mixtures and combinations thereof.

Yet still another embodiment of the present invention is a mixture of any herbicide, fungicide, and insecticide selected form the above groups having improved drift control comprising the surfactant drift control agent in accordance with the invention.

The above listings of specific surfactants and pesticides are not intended to be inclusive of all possibilities.

The invention will now be illustrated by the following non-limiting examples.

We used Sympatec Helos-R series laser diffraction system to measure the droplets distribution during spraying (Spray condition: 40 psi, Teejet 8002 vs. nozzle)

Samples Description:

TABLE 1

The chemicals discussed in the current patent

| | Description |
|---|---|
| Silwet ® L-77 | Polyalkyleneoxide Modified Heptamethyltrisiloxane |
| 2,4-D DMA | 50% a.e. 2,4-D dimethylamine salt, a herbicide |
| Arquad ® 2HT-75 IPA | Di-tallow dimethyl chloride quaternary surfactant, 75% in isopropyl alcohol |
| Arquad ® 2HT-75 PG | Di-tallow dimethyl chloride quaternary surfactant, 75% in propylene glycol |
| Ethomeen ® T/12 | Ethoxylated tallowamine-2EO |
| Ethoquad ® C/12 | Ethoxylated cocoamine-2EO methyl chloride quaternary surfactant |
| Ethoquad ® E/12 | Ethoxylated erucylamine-2EO methyl chloride quaternary surfactant |
| Armeen ® APA T | Tallow dimethylamidopropylamine |
| Ethomeen ® T/20 | Ethoxylated tallowamine-10EO |
| Aromox ® C/12 | Cocoamine oxide with 2 EO (30%? active) |
| DR-200 | Hydroxypropyl modified guar gum |

Example 1: Effect of the Size of Dispersed Particles on Anti-Drift Performance

Pure water produces a lot of fine droplets during spraying (usually 47~50% vol. with size <150 um) which is prone to drift. Adding 0.2% Silwet® L-77 to water formed a hazy dispersion and this dispersion was able to reduce the fine droplets to ~24% (a ~50% reduction in fines). This system is considered to have good anti-drift property. However, after homogenizing, the same hazy sample turn clear and the percent fine droplets produced while spraying the clear sample went back up to 47% (about the same level as water). (See the following table).

TABLE 2

The impact of vesicle size on the spray drift property of Silwet L-77 solution

| Treatment | | Appearance | Vesicle size | Dynamic surface tension | Spray Drift (vol. % < 150 μm) |
|---|---|---|---|---|---|
| Water | | | | High (72) | 47 |
| 0.2% Silwet ® L-77 | Stirred | Hazy/turbid | Large | Low | 24 |
| 0.2% Silwet ® L-77 | Stirred then homogenized | Clear | Small | Lower | 47 |

In this case, the volume percents of the dispersed Silwet® L-77 particles (vesicles) in the stirred only sample and the homogenized sample remained the same because the concentrations of L-77 were the same. The result that a homogenized 0.2% L-77 (clear with small particles) produced as high amount of fines as water while a stirred only 0.2% L-77 (hazy with large particles) produced ~50% less fine droplets during spraying suggests that the particles size in a dispersion plays a key role in determining the fine droplets amount during spraying. The result points out that the spray solution with an anti-drift agent should be properly agitated so as not reduce the particle size too much.

Example 2: Effect of the Concentration of Dispersed Silwet L-77 Particles on Anti-Drift Performance The good anti-drift property of a hazy 0.2% Silwet L-77 could also be lost by adding small amount of certain additives. We observed that the large vesicles present in the stirred only sample of 0.2% Silwet® L-77 (example 1) disappeared (system became clear) after adding small amount (0.05%) 2,4-D DMA ae or many other additives. In this case, adding 2,4-D DMA is believed to modify the microstructure of the dispersed particles so as to decrease the amount of the dispersed particles to such a low concentration that the system became clear. The good anti-drift property of a hazy Silwet® L-77 system lose its anti-drift property when it became clear after adding 2,4-D DMA. The clear L-77 system produced a lot of fines droplets as water did during spraying. Many alcohol ethoxylates with a few ethylene oxide units behaved similarly to Silwet® L-77. We believe the dispersion of alcohol ethoxylates was also a vesicle or liposome dispersion. It is showed in this example that the presence of dispersed droplets (in vesicle or liposome form) is necessary for this dispersion system to exhibit good anti-drift property and the concentration of particles plays an important role in determining the fine droplets amount during spraying.

This example demonstrates that general conclusions about the anti-drift property of a surfactant cannot be drawn. An anti-drift agent such as alcohol ethoxylates can loss their anti-drift property in real pesticide formulations due to the disappearance of the dispersed macrostructure or the turbidity.

Example 3: Effect of the Concentration of Dispersed Quaternary Surfactant Particles on Anti-Drift Performance in DI Water Alone Various samples varying in concentration of Arquad® 2HT (obtained by drying Arquad® 2HT-75 IPA) in DI water were sprayed. The following table showed the impact of Arquad® 2HT concentrations on the % volume of droplets whose size was less than 150 μm. Details are shown in the following table.

TABLE 3

The impact of Arquad ® 2HT quaternary surfactant concentrations on the % volume of droplets whose size was less than 150 μm

| Arquad ® 2HT quaternary surfactant | Appearance | $x_{50}$/ μm | % vol. (<150 mm) | Percent reduction in volume of fine droplets <150 μm when compared to water |
|---|---|---|---|---|
| 3.00% | Turbid | 178 | 39 | 16 |
| 2.00% | Turbid | 193 | 37 | 18 |
| 1.00% | Turbid | 224 | 31 | 32 |
| 0.50% | Turbid | 223 | 30 | 34 |
| 0.25% | Turbid | 234 | 28 | 39 |
| 0.13% | Turbid | 229 | 29 | 37 |
| 0.06% | Turbid | 238 | 28 | 39 |
| 0.03% | Slightly turbid | 240 | 27 | 41 |
| 0.02% | Slightly turbid | 229 | 29 | 36 |
| 0.01% | Slightly turbid | 222 | 29 | 36 |
| 0 (water) | Clear | 162 | 46 | 0 |

The turbidity in the dispersion was caused by the presence of the vesicle or liposome of Arquad 2HT. The results showed that, even at a low concentration of 0.01% Arquad® 2HT, the system was turbid and the spray drift control was very good with a reduction of about 36% of the fine droplets. The drift control ability was pretty constant between studied concentration range between 0.01 and 1% Arquad® 2HT. No increased elongated viscosity, which was deemed to be necessary as disclosed in literature, was apparent in this system. We also measured the size of the dispersed particles by a particle size analyzer based on laser diffraction techniques. The result showed that the patterns of the particle size distribution for this system were similar at different concentration. The distribution mainly had two nominal peaks, one peaked at about 20 μm (much bigger peak) and the other at 200 μm in size.

Example 4: Effect of the Concentration of Dispersed Particles (Arquad® 2HT) on Anti-Drift Performance A milky sample, 5.0% ae 2,4-D DMA+5.0% ai Arquad® 2HT-75 PG, was diluted with water. The fine droplets amount during spraying went through a minimum corresponding to the haziness (appearance) of the sample. The result is shown in the following table.

TABLE 4

Effect of the concentration of dispersed particles (Arquad ® 2HT) and solution appearance on anti-drift performance of a 2,4-D herbicide system.

| wt % ai of Arquad ® 2HT-75PG in 2,4-D system | Appearance | Spray Drift vol. % <150 μm | Comment |
|---|---|---|---|
| 5 | Milky (vesicles) | 55 | Too many particles. Poor anti-drift performance |
| 2.5 | Milky | 42 | Still too many particles. Poor anti-drift performance |
| 1.25 | Milky | 31 | Good anti-drift performance |
| 0.625 | Milky | 30 | Good anti-drift performance |
| 0.3125 | hazy | 29 | Good anti-drift performance |
| 0.15625 | hazy | 28 | Best anti-drift performance |
| 0.078125 | Hazy | 29 | Good anti-drift performance |
| 0.0390625 | slightly hazy | 33 | Number of particles getting a little lower and the system starts to loss anti-drift performance |
| 0.0195 | very slightly hazy | 37 | Number of particles getting even lower and the system lose good anti-drift performance |

This example showed that Arquad® 2HT is useful as an anti-drift agent for a pesticide (e.g., 2,4-D DMA).

The dispersion is a dispersion of di-tallow dimethyl quaternary surfactant in 2,4-D DMA spray solution. We believe the dispersed particles are in the form of vesicles or liposomes.

This result shows again that the amount of vesicles is important in spray drift control. If the number of vesicles is too many, there is no reduction is spray drift. If the number of vesicles is too little indicated by the clarity of the solution, the anti-drift performance is also not good. Only when the number of vesicles is in the right place, the spray drift reduction is significant.

Example 5

Di-tallow dimethyl quaternary surfactant (Arquad 2HT-75 IPA) can produce ~50% reduction in fine droplets (<150 μm, compare sample 1, 6, and 15) in the following table.

TABLE 5

The fine droplet volume (less than 150 μm)
and its appearance in different spray solution

| Sample # | 2,4-D DMA ae wt % | Ethoxylated tallow amine-10EO wt % active | Di-tallow dimethyl quaternary surfactant wt % active | Spray Drift vol. % <150 μm | Spray Solution Appearance |
|---|---|---|---|---|---|
| 1 | 1.2 | 0.2 | 0.6 | 25.77 | Turbid |
| 2 | 1.0 | 0.4 | 0.6 | 30.67 | Turbid |
| 3 | 1.3 | 0.3 | 0.4 | 27.57 | Turbid |
| 4 | 1.4 | 0.2 | 0.4 | 27.69 | Turbid |
| 5 | 1.0 | 0.5 | 0.5 | 30.91 | Turbid |
| 6 | 1.2 | 0.4 | 0.4 | 25.75 | Turbid |
| 7 | 1.4 | 0.3 | 0.3 | 29.01 | Turbid |
| 8 | 1.6 | 0.2 | 0.2 | 27.55 | Turbid |
| 9 | 0.8 | 0.6 | 0.6 | 28.54 | Turbid |
| 10 | 0.6 | 0.7 | 0.7 | 29.36 | Turbid |
| 11 | 0.2 | 1.4 | 0.4 | 31.43 | Turbid |
| 12* | 0.4 | 1.4 | 0.2 | 32.95 | Turbid |
| 14 | 0.4 | 0.4 | 1.2 | 38.67 | Turbid |
| 15 | 0.8 | 0.1 | 1.1 | 54.81 | Clear |
| 16 | | 2.0 | | 50 | Turbid |
| 17 | | | 2.0 | 42 | Clear |

*The appearance of freshly made #12 sample was Turbid and the spray data showed only 32.95% of the spray droplet was under 150 micron. However, it turned clear when the sample was stored at room temperature overnight. The spray data showed the volume of spray droplet under 150 micron was same as 2,4-D DMA alone.

The microstructures (vesicles) were detected under the light-microscopic only for the samples showing a good drifting control property. The following picture is the microstructure captured for sample #1 in table 5.

FIG. 1: The microstructure captured under the light microscope for sample #1 in table 5

The size of the marked particles shown in the picture ranged from ~45 to ~2. The very small particles couldn't be measured accurately with the light-microscope.

Figure 2:
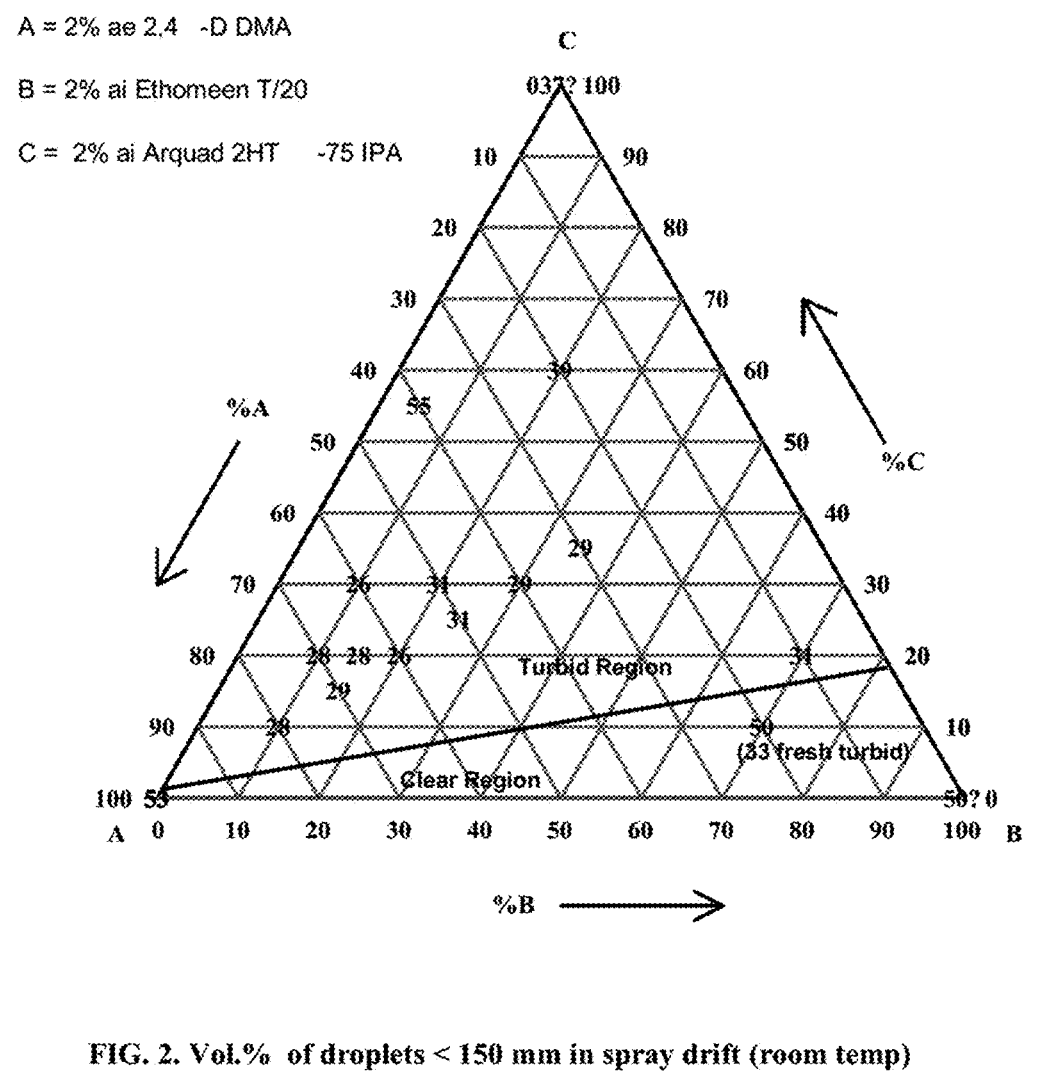

The data can also be plotted in the following phase diagram format (FIG. 2).

In the phase diagram, the region below the phase boundary curve was clear. In this region, there was no reduction in fine droplets compared to water. At composition 20:70:10, the initial sample was hazy and the % fine droplet was 33%. However, after overnight, the sample turn clear and the % fine droplet became 50% (i.e., no reduction in fine droplets vs. water). In the region above the phase boundary, the samples were hazy due to the presence of vesicles. However, not all compositions in this hazy region possess the ability to reduce fine droplets (e.g., composition 40:5:55). The best fine droplet reduction region was found to be around composition 60:10:30.

One of the components used in this example, Ethomeen® T/20, is an alkylamine ethoxylate which is a common adjuvant for glyphosate which is the most popular tank mix herbicide. As it is shown in the phase diagram, Ethomeen T/20 itself doesn't have drift control property in this system. In fact, Ethomeen T/20 can disrupt the formation of the macrostructure such as vesicle or liposome produced by many drift control surfactant systems, rendering the surfactant useless in controlling the drift. The result showed in this example demonstrates that Arquad 2HT is capable of controlling the drift even in the presence of alkylamine ethoxylate.

The presence of glyphosate in this example didn't affect the spray drift result very much. The drift reduction was only affected by the surfactant concentration and composition.

It is again showed that the presence of dispersed droplets (in vesicle or liposome form), or the presence of haziness, is necessary for this system to exhibit good anti-drift property.

Example 6: The Effect of Arquad 2 HT on the Drift Potential of 2,4-D DMA and Roundup® Weather Max Systems

TABLE 6

The effect of Arquad 2 HT on the drift potential of 2,4-D DMA and Roundup ® Weather Max systems

| 2,4-D DMA, % a.e. | Roundup ® WeatherMax, % a.e. | Arquad ® 2 HT, % a.i | System appearance | Vol. % reduction of fine droplets <150 μm from water |
|---|---|---|---|---|
| 0 | 1.0 | 0 | Clear | −3 |
| 1.0 | 0 | 0 | Clear | 8 |
| 0.85 | 0.9 | 0.25 | cloudy | 19 |
| 0.85 | 0.9 | 0.5 | cloudy | 13 |
| 0.85 | 0.9 | 1.0 | cloudy | −19 |

It is showed that the presence of dispersed droplets (in vesicle or liposome form) is necessary for this dispersion system to exhibit good anti-drift property, however, the concentration of the surfactant was also critical for optimize the drift reduction property.

Example 7: Effect of Various Surfactants and Surfactant Blends on Droplet Size During Spraying 1% 2,4-D DMA System

TABLE 7

Individual Surfactants Effect on Spray Droplet size Distribution (0.025% surfactant in 1% a.e. 2,4-D DMA)

| 2,4-D DMA | Surfactant | Appearance | Mean (μm) | Vol. % Reduction of fine droplets <150 μm from water |
|---|---|---|---|---|
| 1.0% a.e. | None | clear | 163.21 | −5 |
| 1.0% a.e. | 0.025% a.i. Ethoquad ®E 12/75 | clear | 164.77 | −7 |
| 1.0% a.e. | 0.025% a.i. Aromox ® APA TW | clear | 143.58 | −21 |
| 1.0% a.e. | 0.025% a.i. Ethomeen ® T/12 | clear | 170.80 | −3 |
| 1.0% a.e. | 0.025% a.i. Aromox ®APA EE | clear | 152.46 | −14 |

The data showed that individual surfactant alone was not able to reduce the amount of fine droplets in 1% a.e. 2,4-D DMA because the spray solutions were clear (no dispersed particles).

TABLE 8

Effect of Surfactant Blend on Particle Size Distribution
(0.025% surfactants in 1% a.e. 2,4-D DMA)

| # | Surf1:Surf2 | Total Surf (%) | Ratio (surf1:surf2) | Vol. % Reduction of fine droplets <150 μm from water |
|---|---|---|---|---|
| 1 | 2,4-D DMA alone | | | −8 |
| 10 | Ethoquad ® E 12/75:Aromox ® C/12 | 0.025 | 95:5 | 32 |
| 11 | Ethoquad ® E 12/75:Aromox ® C/12 | 0.025 | 90:10 | 37 |
| 12 | Ethoquad ® E 12/75:Aromox ® C/12 | 0.025 | 85:15 | 34 |
| 13 | Ethoquad ® E 12/75:Ethomeen ® T/12 | 0.025 | 95:5 | 31 |
| 14 | Ethoquad ® E 12/75:Ethomeen ® T/12 | 0.025 | 90:10 | 28 |
| 15 | Ethoquad ® E 12/75:Ethomeen ® T/12 | 0.025 | 85:15 | 27 |
| 23 | Ethoquad ® E 12/75:Aromox ® APA-TW | 0.025 | 95:5 | 23 |
| 22 | Ethoquad ® E 12/75:Aromox ® APA-TW | 0.025 | 90:10 | 27 |
| 24 | Ethoquad ® E 12/75:Aromox ® APA-TW | 0.025 | 85:15 | 26 |

All samples except #1were a little hazy.

This example shows that the combination of surfactant is critical to achieve good drift control.

Example 8

The amount of fine droplets during spraying of a diluted latex product (Primal® AC261 high gloss latex paint, studied concentration range 0.2%-2.0%) was studied. The data in this example shows that the amount of permanent spheres (latex particles) or presence of solid particles does not contribute to reduction of fine droplets in a spray solution. That is, it further demonstrated that the presence of non-permanent dispersed droplets such as vesicle (or liposome) is necessary for a dispersion system to exhibit good anti-drift property.

TABLE 9

The concentration effect of Primal AC261 on
the fine deduction of the spray solutions.

| Spray Solution concentration of Primal ® AC261 | Mean of the droplet (um) | % Reduction of fine droplets <150 μm (vol . %) from water |
|---|---|---|
| 2.0% | 148.71 | −4 |
| 1.0% | 147.89 | −4 |
| 0.5% | 150.44 | −2 |
| 0.25% | 150.46 | −2 |
| 0.1% | 160.62 | 5 |

The data demonstrate that the necessary conditions for a spray solution to have significant fine droplets (<150 micron) number reduction are (1) the spray must possess some turbidity, and (2) the turbidity must come from a non-permanent dispersed phase comprising a surfactant in water.

What is claimed is:

1. An aqueous agrochemical spray solution comprising at least one agrochemical active and at least one surfactant, wherein said at least one surfactant comprises an alkyl dimethylamidopropylamine oxide or an alkyl dimethylamidopropylamine betaine, wherein the alkyl group is a C12-C22, saturated or non-saturated, linear or branched alkyl group derived from the oil of coco, soy, palm, castor, tallow, corn, lard, peanut or tall, including the epoxydized version of the oil, wherein said spray solution comprises a dispersed phase comprising dispersed particles which have an average particle size between 1 to 100 microns, wherein the concentration of said dispersed particles is from about 0.001 to 5 wt %, wherein said aqueous agrochemical spray solution is capable of reducing the volume of the fine droplets in mist whose size is less than 150 microns during spraying by at least 20% compared to the same aqueous spray solution without the presence of the said surfactant, and wherein said aqueous agrochemical spray solution does not comprise either (a) a tertiary amine surfactant of the formula:

$$R^1 \diagdown N \diagup R^3 \atop | \atop R^2$$

wherein $R^1$ represents a straight or branched chain ($C_{12}$-$C_{22}$) alkyl and $R^2$ and $R^3$ independently represent a straight or branched chain ($C_1$-$C_{22}$) alkyl; or (b) a tertiary amine oxide surfactant of the formula:

$$R^4 \diagdown N^+ \diagup R^6 \atop | \atop R^5 \atop O^-$$

wherein $R^4$ is a straight or branched chain ($C_{10}$-$C_{22}$) alkyl or an alkyletherpropyl, and $R^5$ and $R^6$ independently are straight or branched chain ($C_1$-$C_{22}$) alkyl or ethoxylates or propoxylates of the formula:

$$\{C_2H_4O\}_n H \quad \text{or} \quad \{C_2H_3(CH_3)O\}_n H$$

wherein n is an integer from 1 to 20.

2. The aqueous agrochemical spray solution of claim 1, wherein the at least one agrochemical active is a herbicide.

3. The aqueous agrochemical spray solution of claim 2, wherein the said herbicide comprises a salt of glyphosate, a salt of 2,4-D, a salt of dicamba, a salt of glufosinate, or a combination and/or mixture thereof.

4. The aqueous agrochemical spray solution of claim 1, wherein the dispersed particles are vesicles or liposomes formed by said at least one surfactant.

5. The aqueous agrochemical spray solution of claim 1, wherein the alkyl group of the surfactant is C16-C22.

6. An agrochemical formulation comprising an active ingredient and at least one surfactant, wherein said at least one surfactant comprises an alkyl dimethylamidopropylamine oxide or an alkyl dimethylamidopropylamine betaine, wherein the alkyl group is a C12-C22, saturated or non-saturated, linear or branched alkyl group derived from the oil of coco, soy, palm, castor, tallow, corn, lard, peanut or tall, including the epoxydized version of the oil, wherein the said agrochemical formulation is capable of forming a aqueous agrochemical spray solution containing a dispersed phase comprising dispersed particles which have an average particle size between 1 to 100 microns, wherein the concentration of said dispersed particles is from about 0.001 to 5 wt %, wherein said aqueous spray solution is capable of reducing the volume of the fine droplets in mist whose size is less than 150 microns during spraying by at least 20% compared to the same aqueous spray solution without the presence of the said surfactant, and wherein said aqueous agrochemical spray solution does not comprise either (a) a tertiary amine surfactant of the formula:

$$R^1\diagdown N(R^2)\diagup R^3$$

wherein $R^1$ represents a straight or branched chain ($C_{12}$-$C_{22}$) alkyl and $R^2$ and $R^3$ independently represent a straight or branched chain ($C_1$-$C_{22}$) alkyl; or (b) a tertiary amine oxide surfactant of the formula:

$$R^4\diagdown \underset{O^-}{N^+(R^5)}\diagup R^6$$

wherein $R^4$ is a straight or branched chain ($C_{10}$-$C_{22}$) alkyl or an alkyletherpropyl, and $R^5$ and $R^6$ independently are straight or branched chain ($C_1$-$C_{22}$) alkyl or ethoxylates or propoxylates of the formula:

$$\text{-}[C_2H_4O]_n\text{-}H \quad \text{or} \quad \text{-}[C_2H_3(CH_3)O]_n\text{-}H$$

wherein n is an integer from 1 to 20.

7. The formulation of claim 6, wherein the aqueous agrochemical comprises a herbicide.

8. The formulation of claim 7, wherein the said herbicide comprises a salt of glyphosate, a salt of 2,4-D, a salt of dicamba, a salt of glufosinate, or a combination and/or mixture thereof.

9. The formulation of claim 6, wherein the dispersed particles are vesicles or liposomes formed by said at least one surfactant.

10. The formulation of claim 6, wherein the alkyl group of the surfactant is C16-C22.

11. A method of reducing the spray drift of an aqueous agrochemical spray solution upon spraying with a spraying apparatus, which comprises adding at least one surfactant to said aqueous agrochemical spray solution in an amount effective to form a dispersed phase comprising dispersed particles which have an average particle size between 1 to 100 microns, wherein said at least one surfactant comprises an alkyl dimethylamidopropylamine oxide or an alkyl dimethylamidopropylamine betaine, wherein the alkyl group is a C12-C22, saturated or non-saturated, linear or branched alkyl group derived from the oil of coco, soy, palm, castor, tallow, corn, lard, peanut or tall, including the epoxydized version of the oil, wherein the concentration of said dispersed particles is from about 0.001 to 5 wt %, wherein said aqueous spray solution is capable of reducing the volume of the fine droplets in mist whose size is less to than 150 microns during spraying by at least 20% compared to the same aqueous spray solution without the presence of the said surfactant, and wherein said aqueous agrochemical spray solution does not comprise either (a) a tertiary amine surfactant of the formula:

$$R^1\diagdown N(R^2)\diagup R^3$$

wherein $R^1$ represents a straight or branched chain ($C_{12}$-$C_{22}$) alkyl and $R^2$ and $R^3$ independently represent a straight or branched chain ($C_1$-$C_{22}$) alkyl; or (b) a tertiary amine oxide surfactant of the formula:

$$R^4\diagdown \underset{O^-}{N^+(R^5)}\diagup R^6$$

wherein $R^4$ is a straight or branched chain ($C_{10}$-$C_{22}$) alkyl or an alkyletherpropyl, and $R^5$ and $R^6$ independently are straight or branched chain ($C_1$-$C_{22}$) alkyl or ethoxylates or propoxylates of the formula:

$$\text{-}[C_2H_4O]_n\text{-}H \quad \text{or} \quad \text{-}[C_2H_3(CH_3)O]_n\text{-}H$$

wherein n is an integer from 1 to 20.

12. The method of claim 11, wherein the aqueous agrochemical comprises a herbicide.

13. The method of claim 12, wherein the said herbicide comprises a salt of glyphosate, a salt of 2,4-D, a salt of dicamba, a salt of glufosinate, or a combination and/or mixture thereof.

14. The method of claim 11, wherein the dispersed particles are vesicles or liposomes formed by said at least one surfactant.

15. The method of claim 11, wherein the alkyl group of the surfactant is C16-C22.

* * * * *